US00PP31498P2

(12) United States Plant Patent
Egger

(10) Patent No.: US PP31,498 P2
(45) Date of Patent: Feb. 25, 2020

(54) ***PENSTEMON* PLANT NAMED 'TNPENHM'**

(50) Latin Name: ***Penstemon* hybrid**
Varietal Denomination: TNPENHM

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,945

(22) Filed: Feb. 4, 2019

(51) Int. Cl.
*A01H 5/02* (2018.01)
*A01H 6/68* (2018.01)

(52) U.S. Cl.
USPC ..... Plt./465
CPC ..... *A01H 6/68* (2018.05)

(58) Field of Classification Search
USPC ..... Plt./465
See application file for complete search history.

*Primary Examiner* — Anne Marie Grunberg
(74) *Attorney, Agent, or Firm* — Klarquist Sparkman, LLP

(57) ABSTRACT

A new and distinct *Penstemon* plant is characterized by medium-size, red-pink flowers with white throats in dense clusters; long bloom time; good rebloom; a compact, upright, well-branched habit with multiple crown from the base; clean-looking, deep-green, attractive foliage; and excellent vigor.

1 Drawing Sheet

Botanical denomination: *Penstemon* hybrid.
Variety designation: 'TNPENHM'.

BACKGROUND OF THE INVENTION

The present invention relates to a new and distinct *Penstemon* plant given the name 'TNPENHM'. *Penstemon* is in the family Scrophulariaceae. *Penstemon* 'TNPENHM' originated from open-pollinated seeds of *Penstemon* '165-3', an unnamed, unpatented, proprietary plant. It was part of a controlled breeding program to create a compact, upright, medium- to small-size, reblooming, and hardy series. This seedling was selected for its medium-size red-pink flowers with white throats; flowers in dense clusters; long bloom time; good rebloom; compact, upright, well-branched habit with multiple crowns from the base; vigor; and clean, attractive look. It is an ideal plant for a sunny border in full sun.

SUMMARY OF THE INVENTION

The present invention has not been evaluated under all possible environmental conditions. The phenotype may vary with variations in environment without a change in the genotype of the plant.

*Penstemon* 'TNPENHM' is uniquely distinguished by its:

1. medium-size red-pink flowers with white throats in dense clusters,
2. long bloom time,
3. good rebloom,
4. compact, upright, well-branched habit with multiple crowns from the base,
5. clean-looking, deep-green, attractive foliage, and
6. excellent vigor.

Compared to the seed parent, *Penstemon* '165-3', the new plant has red-pink flowers, rather than hot pink, and is more upright.

Compared to *Penstemon* x *mexicali* 'P008S', an unpatented plant, the new plant has larger and more numerous flowers that are red-pink with white throats, rather than purple-pink with white throats.

Compared to *Penstemon* 'Boysenberry Taffy' (U.S. Plant Pat. No. 25,361), the new plant has a shorter habit; skinnier leaves; pinker flowers, rather than red-purple; and a more narrow-upright habit.

Compared to *Penstemon* 'Cha Cha Hot Pink' (U.S. Plant Pat. No. 26,699), the new plant has a shorter habit; narrower leaves; a narrow-upright habit, rather than wide and mound-like; and more pronounced white throats.

Trade Designation: HARLEQUIN™ Magenta.

The new variety has been reproduced only by asexual propagation (cuttings and micropropagation). Each of the progeny exhibits identical characteristics to the original plant. Asexual propagation by cuttings and micropropagation using terminal and lateral shoots, as done in Canby, Oreg., shows that the foregoing characteristics and distinctions come true to form and are established and transmitted through succeeding propagations.

DETAILED PLANT DESCRIPTION

Figure 1:
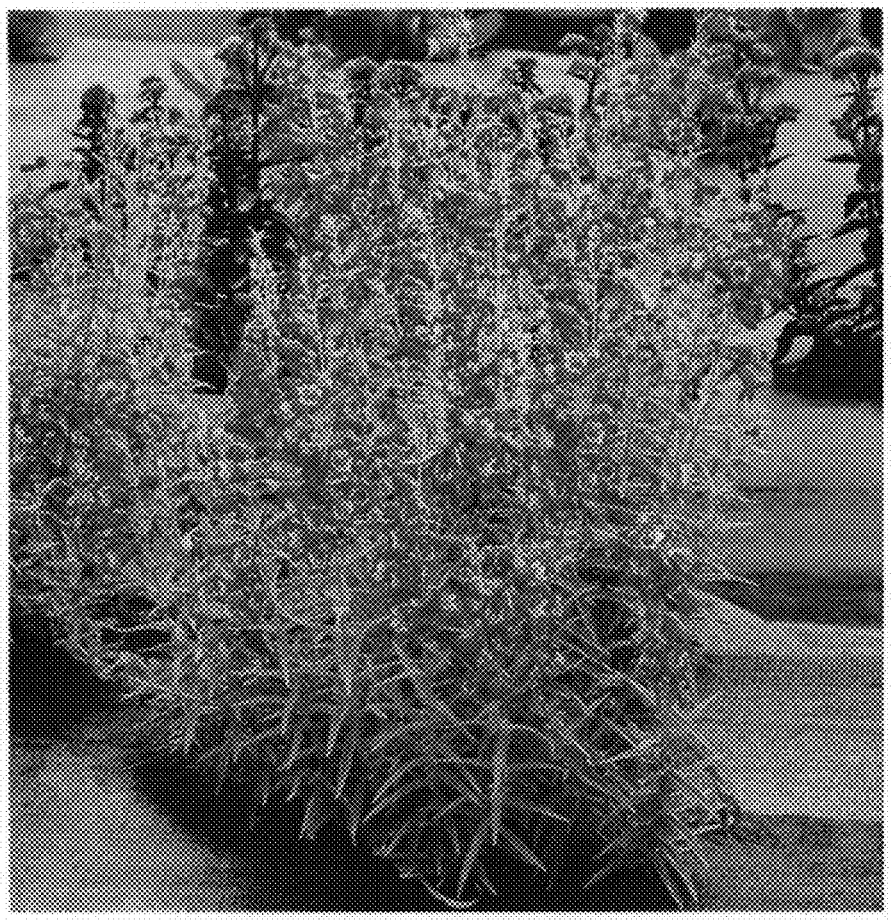
FIG. 1 shows a close up of the new plant as a 12-month-old in a trial field in full bloom in August in Canby, Oreg.
Figure 2:
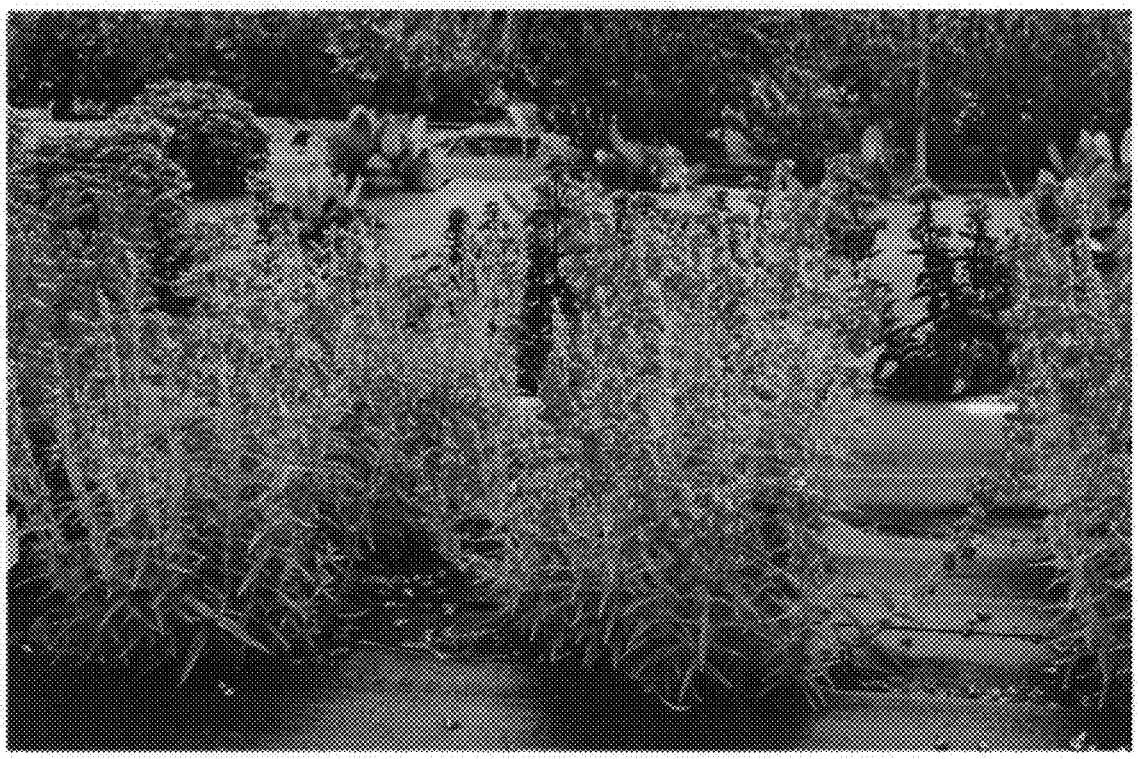
FIG. 2 shows the habit of the 12-month-old plant in FIG. 1.

The following is a detailed description of the new *Penstemon* plant based on observations of 2-year-old specimens grown outside in a trial field in full sun in Canby, Oreg. in October. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart,* 5th edition, 2007.

Plant:

*Type*.—Herbaceous perennial.

*Form*.—Upright, branching.

*Cold hardiness*.—USDA Zone 6-10.

*Size*.—Grows to 50 cm wide and 54 cm high.

*Vigor*.—Excellent.

*Stem number*.—About 20 main stems from the crown.

*Stem strength*.—Strong.

*Stem*.—Strongly upright, branched with branches strongly upright, grows to 24 cm long to the main inflorescence and 5 mm wide (at the base), glabrous, internodes grow to 2 cm long, Yellow Green 146B to Grey Brown N199A at base.

*Roots and rooting*.—Fibrous root system, White 155C, roots easily from stem cuttings in 10 to 14 days.

Leaf:

*Type*.—Simple.

*Arrangement*.—Opposite.

*Shape*.—Lanceolate.

*Venation*.—Pinnate, main vein on top Greyed Orange 177D and bottom side Yellow Green 145C.

*Margins*.—Serrulate.

*Apex*.—Acuminate.

*Base*.—Sessile.

*Petiole*.—None, sessile.

*Blade size*.—Grows to 8 cm long and 1.5 cm wide.

*Surface texture*.—Glabrous on both sides.

*Leaf color*.—Topside Green 137B, bottom side closest to Yellow Green 147B.

Inflorescence:

*Type*.—Terminal, many flowered, dense thyrse.

*Number of flowers per inflorescence*.—20 to 76.

*Size of inflorescence*.—Grows to 27 cm long and 8 cm wide.

*Peduncle*.—Strong, upright, grows to 3 cm long and 3 mm wide, glandular pubescent, Yellow Green 146B.

*Pedicel*.—Medium strength, grows semi-upright to 1 cm long and 1 mm wide, glandular pubescent, Yellow Green 146C in shade and lightly tinted Greyed Purple 187B in sun.

*Bloom period*.—Mid-June to frost in November in Canby, Oreg. if spent flowers are removed.

Flower bud:

*Size*.—2.5 cm long and 12 mm wide.

*Description*.—Closed tubular, bulging, flattened centrically, pubescent.

*Color*.—Purple 71A.

Flower:

*Type*.—Zygomorphic, perfect.

*Shape*.—Tubular, bilabiate.

*Size*.—Grows to 3.2 cm long and 3 cm wide.

*Corolla description*.—Grows to 3.4 cm long and 3.2 cm wide; tube is bulbous in the calyx for 6 mm long and 5 mm wide, narrowing then widening for 20 mm and flaring to 32 mm wide, 5 to 8 lobes; when 5 lobes, the top lobe is 9 mm wide and 10 mm long, side 2 lobes are 8 mm wide and 10 mm long, and the bottom 2 lobes are 8 mm wide and 10 mm long; with 8 lobes, the top 2 lobes overlap and flare back slightly (8 mm wide and 10 mm deep), two larger lateral lobes curl back (8 mm wide and 10 mm deep), and the four lower lobes flare back (each 6 mm wide and to 8 mm deep); lobe margins entire, tips obtuse; outside glandular pubescent, inside sparsely pubescent; outside color Purple 71A on top tube and all lobes, bottom tube Violet 85A; inside color lobes Purple 71A, tube Violet 85C on top and 85C streaked with N79C on bottom and sides.

*Calyx description*.—8 mm deep and 8 mm wide, 5 lobes cut to the base; lobes lanceolate, 8 mm deep and 2.5 mm wide; margins entire; tip acuminate; base cuneate; outside Yellow Green 146C tinted Greyed Purple 187A where in sun; inside Yellow Green 146C; both sides pubescent.

*Pistil description*.—1, 20 mm long, ovary 4 mm long and 2 mm wide, Yellow Green 146D; style 15 mm long and less than 1 mm wide, style White NN155C; stigma flattened, White NN155C.

*Stamen description*.—5, one sterile without an anther, held within the corolla 20 mm long; filaments 18 to 22 mm long and less than 1 mm wide, White NN155C; anthers horseshoe-shaped, 2 mm long and 2 mm wide, Red Purple 70A; pollen amount moderate, White NN155C.

*Fragrance*.—None.

*Lastingness*.—A flower lasts 5 to 6 days.

Fruit:

*Type*.—Capsule.

*Fertility*.—Poor.

*Size*.—7 mm deep and 5 mm wide.

*Texture*.—Glabrous.

*Color*.—Brown N199C.

Seed:

*Shape*.—Irregular.

*Size*.—1 mm long.

*Texture*.—Glabrous.

*Color*.—Brown 200A.

Pests and diseases: The new plant is typical to the genus. No problems have been found in Canby, Oreg.

I claim:

1. A new and distinct *Penstemon* plant as illustrated and described.

* * * * *